United States Patent

Shang et al.

[11] 3,945,804
[45] Mar. 23, 1976

[54] AMMOXIDATION APPARATUS

[75] Inventors: Jer-Yu Shang, Wilmington, Del.;
Raymond Wynkoop, Gladwyne, Pa.

[73] Assignee: Sun Ventures, Inc., St. Davids, Pa.

[22] Filed: June 24, 1974

[21] Appl. No.: 482,060

Related U.S. Application Data

[62] Division of Ser. No. 286,634, Sept. 6, 1972, Pat. No. 3,846,473.

[52] U.S. Cl............... 23/288 E; 23/252 R; 23/284; 23/288 B; 239/102; 261/78 A; 261/DIG. 48
[51] Int. Cl.² ............................................. B01J 8/10
[58] Field of Search .. 23/284, 252 R, 288 B, 288 E; 261/78 A, DIG. 48; 239/102

[56] References Cited

UNITED STATES PATENTS

| | | | |
|---|---|---|---|
| 2,392,798 | 1/1946 | Kleiss | 23/288 E X |
| 3,038,532 | 6/1962 | Eisenkraft | 239/102 X |
| 3,234,013 | 2/1966 | Phillips et al. | 23/284 X |
| 3,505,018 | 4/1970 | Bawa et al. | 23/284 X |
| 3,677,525 | 7/1972 | Schurig et al. | 239/102 X |
| 3,720,290 | 3/1973 | Lansky et al. | 239/102 X |
| 3,860,173 | 1/1975 | Sata | 239/102 |

OTHER PUBLICATIONS

Perry's Chemical Engineers' Handbook, 4th ed., 1963, pp. 5-39.

*Primary Examiner*—Joseph Scovronek
*Assistant Examiner*—Barry I. Hollander
*Attorney, Agent, or Firm*—Donald R. Johnson; Paul Lipsitz

[57] ABSTRACT

A process for vapor phase ammoxidation of hydrocarbons which comprises reacting vapors of ammonia and said hydrocarbon in the presence of a molten salt eutectic mixture of $V_2O_5$ and $K_2O$, said molten salt being atomized in the presence of said ammonia and hydrocarbon, and, optionally, said spent molten salt being regenerated by air oxidation and recycled for reuse. The invention also embodies an apparatus for the ammoxidation process which comprises a reactor vessel fitted with (a) input means for ammonia and hydrocarbon, (b) an atomizing apparatus within said reactor, (c) means for feeding the molten eutectic salt from an upper reservoir to said atomizing apparatus, (d) a lower reservoir for spent molten salt, and (e) a gas-lift to move said spent salt from said lower reservoir to said upper reservoir.

2 Claims, 1 Drawing Figure

U.S. Patent    March 23, 1976    3,945,804
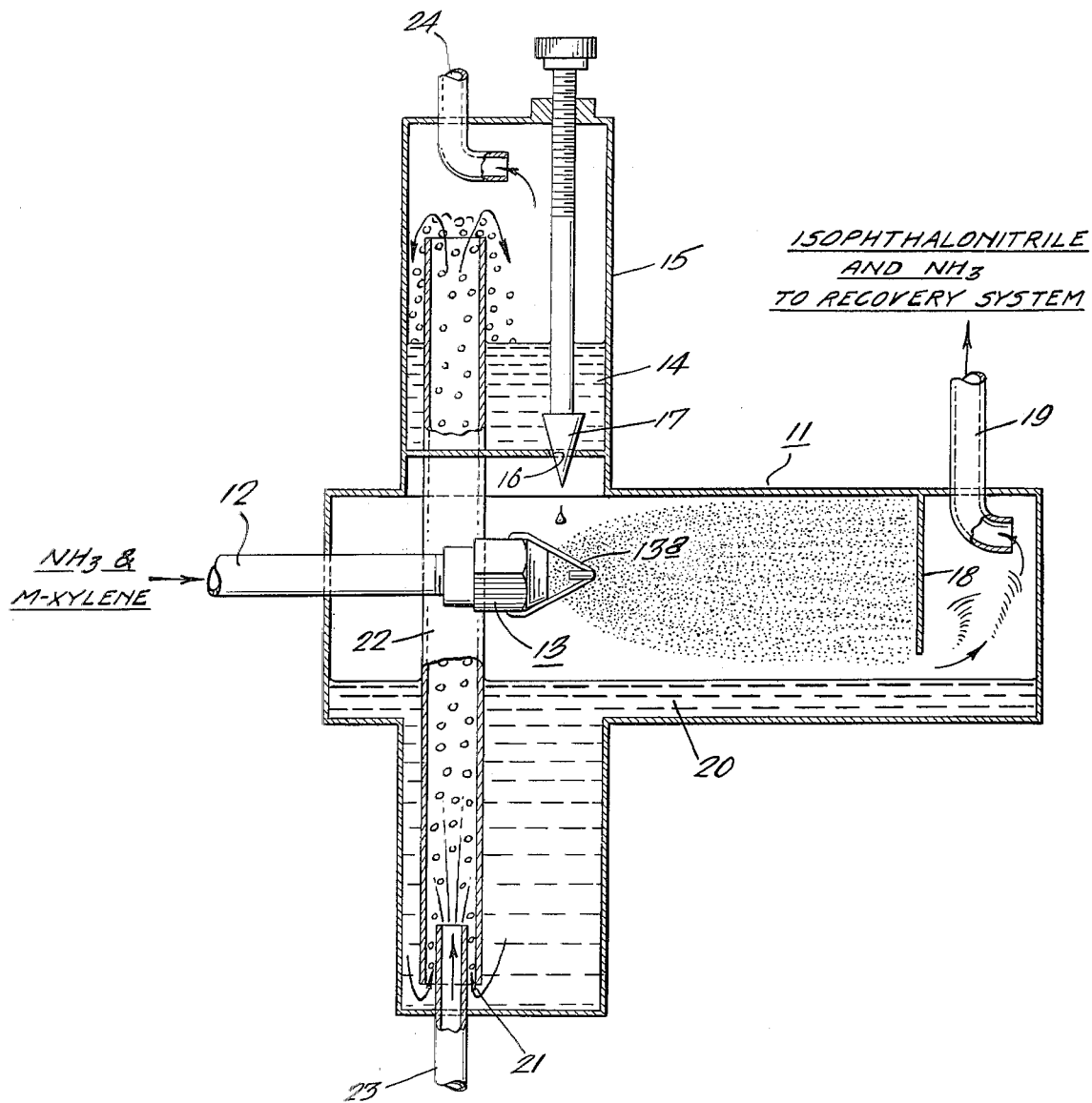

AMMOXIDATION APPARATUS

This application is a divisional application of Ser. No. 286,634, filed Sept. 6, 1972, and now U.S. Pat. No. 3,846,473.

It has been disclosed in the application of William C. Neikam et al., Ser. No. 267,303, filed June 29, 1972, now U.S. Pat. No. 3,812,171, issued May 21, 1974, that ammoxidation reactions may be carried out with $V_2O_5$ as catalyst where the $V_2O_5$ is employed in the form of a molten eutectic with $K_2O$. The eutectic melts at 390°C and consists of 39 mole percent of $K_2O$ and 61 mole percent of $V_2O_5$. It is made simply by heating such a molar mixture slowly with stirring to about 500°C, $CO_2$ being evolved and the eutectic formed. This eutectic is described in an article by Holtzberg, J.A.C.S. 78 p. 1538, 1956.

This invention provides an improved process for carrying out ammoxidation reactions using the above-described eutectic as catalyst. In accord with this invention, there is provided a process for vapor phase ammoxidation of hydrocarbons which comprises reacting vapors of ammonia and said hydrocarbon in the presence of a molten salt eutectic mixture of $V_2O_5$ and $K_2O$, said molten salt being atomized in the presence of said ammonia and hydrocarbon. In a preferred process, the spent molten salt is regenerated by air oxidation and recycled for reuse. The invention also embodies an apparatus for the ammoxidation process which comprises a reactor vessel fitted with (a) input means for ammonia and hydrocarbon, (b) an atomizing apparatus within said reactor, (c) means for feeding the molten eutectic salt from an upper reservoir to said atomizing apparatus, (d) a lower reservoir for spent molten salt, and (e) a gas-lift to move said spent salt from said lower reservoir to said upper reservoir.

The organic reactants useful in the process may be selected from a wide variety of compounds and will include alkyl-substituted aromatic, aliphatic, alicyclic, and heterocyclic compounds. Among preferred starting materials are the mono- and polyalkyl-substituted aromatic hydrocarbons such as toluene, the xylenes, α-methylnaphthalene, polymethylnaphthalenes, monoalkyl and polyalkyl anthracenes, mesitylene, durene, and the like. The alkyl substituent may, of course, contain more than a single atom and thus the corresponding ethyl and other lower alkyl substituents are also useful.

Aliphatic compounds normally subjected to ammoxidation include the olefinic compounds. Thus, any olefinic hydrocarbon having at least one alkyl group is useful in the process. Examples of such compounds are propylene, butenes, octenes, methyl heptenes, alkylbutadienes, pentadienes, ethyl butenes, hexadienes, heptadienes, and the like, all of which will give the corresponding nitriles. Preferred olefins are those containing up to about ten carbon atoms, particularly propylene, butenes, and the methyl-butadienes and cycloolefinic compounds, particularly the alkyl-substituted hydrocarbon olefins exemplified by 3-methyl cyclohexene, 3,6-dimethyl cyclohexene, methyl tetralin and the like.

Also of value as reactants are alicyclic compounds having an alkyl substituent and these compounds are exemplified by methylcyclopentane, methylcyclohexane, the alkyl-substituted decalins, and the like.

The heterocyclic compounds useful as organic reactants in the process will include alkyl-substituted furans, pyrroles, indoles, thiophenes, pyrazoles, imidazoles, thiazoles, oxazoles, pyrans, pyridines, quinolines, isoquinolines, pyrimidines, pyridazines, pyrazines, and the like, all of which are converted to the corresponding nitriles. Preferred reactants in this group are the mono-, di- and tri-alkyl pyridines.

In order to further describe the invention, reference is now made to the drawing and for illustrative purposes the process described will refer to the reaction of meta-xylene and ammonia to yield isophthalonitrile.

In accord with the drawing, ammonia and m-xylene are introduced to a reactor 11 through an input line 12, the mixture of gases passing through a nozzle 13. This nozzle may be of a variety of atomizing devices and is preferably an atomizing type using high intensity sound waves. The nozzle used will provide means for the molten catalyst of the $V_2O_5/K_2O$ eutectic 14 to enter the sonic energy field 13a in order that thorough atomization of the reactants and catalyst occur thus effecting a highly efficient contact and reaction system. Such a nozzle is described in U.S. Pat. No. 3,371,869 and is commercially available under the trade name "Sonicore" from Sonic Development Corporation. The molten eutectic 14 is held in an upper reservoir 15 and is fed into the sonic area of the nozzle through an opening 16 controlled by a valve 17, the rate at which the molten eutectic drops into the nozzle depending upon the size of the opening. The spray from the nozzle may be directed at an optional baffle 18, which will aid in separating the eutectic from the gaseous products. The products of isophthalonitrile, unreacted ammonia, and any by-products are taken overhead through a vent 19 to a separation and product recovery system which may be a series of cyclones (not shown) or other applicable system.

The molten spent eutectic catalyst drops to the bottom of the reaction chamber 11 and is maintained as a liquid lower reservoir 20. Extending from above the bottom of the lower reservoir to a level in the upper reservoir 15 above the molten eutectic is a conduit 22 which serves as a gas-lift and regeneration system for the spent eutectic. Air or other oxygen containing gas is fed into the gas-lift conduit 22 through inlet 23 which is inside and concentric with the conduit and in this way the molten eutectic 21 near the opening of the gas-lift conduit is swept into the gas-lift and transported upward to spill over the conduit into the upper reservoir 15. During its passage through the conduit 22 the oxygen in the lift-gas effects regeneration of the spent eutectic so that it is again ready for use. The lifting gas exits overhead through vent 24.

It will be understood that various alternative methods are useful within the context of the above-described apparatus. For example, the eutectic may be atomized by passing an inert gas through the sonic nozzle and the ammonia and hydrocarbon gases fed into the reaction system separately. Means other than the illustrated valve 17 may be used to feed the molten eutectic to the atomizing nozzle and other modifications will be evident to the skilled art worker.

Because the molten eutectic is highly corrosive it is important that corrosion resistant materials be used throughout the apparatus. The nozzle is particularly sensitive to dimensional change due to corrosion and it is therefore preferred that it be constructed of a highly resistant alloy such as one consisting of 50% nickel and 50% chromium.

The conditions of reaction will be those usually used in the ammoxidation of hydrocarbons. Thus the reaction will be held at a temperature of from about 400° to about 500°C, the usual ammoxidation temperature range. Reaction pressure is preferably atmospheric pressure, although higher and lower pressures may be used (e.g., from about 0.5 to about 20 atmospheres). The products of the reaction, together with any unconverted reactants, after removal from the reactor are separated by conventional methods, any unreacted hydrocarbon being recycled to the reactor, if desired. Similarly, recycle of partially ammoxidized hydrocarbons (e.g., m- or p-xylene converted to m- or p-toluonitrile) may be recycled for further conversion to polynitriles. The rate of ammonia to xylene to hydrocarbon, while not a critical parameter, should be at least about 3 moles of ammonia per mole of hydrocarbon group to be converted to nitrile. In general, an ammonia to hydrocarbon ratio of from about 3:1 to about 12:1 will be employed and such ratios are consistent with the prior art ammoxidation processes. It will be understood that the usual reaction conditions and techniques of prior art ammoxidation processes may be used with the process of this invention.

The invention claimed is:

1. An apparatus for an ammoxidation process which comprises in combination a reactor vessel fitted with (a) input means for vapors of ammonia and hydrocarbon to supply said vapors to an atomizing apparatus within said reactor, (b) an upper reservoir for a molten eutectic salt catalyst, (c) means for feeding said molten eutectic salt from said upper reservoir to said atomizing apparatus, (d) a lower reservoir for spent molten salt, (e) a gas-lift having an inlet for an oxygen containing gas at the bottom of said lower reservoir to move said spent salt from said lower reservoir to said upper reservoir, (f) a vent from said upper reservoir to provide an exit for said lifting gas, and (g) an outlet from said reactor for removing the products of reaction between the ammonia and hydrocarbon.

2. An apparatus as in claim 1 where the atomizing apparatus is a sonic energy device.

* * * * *